United States Patent [19]

Fujii et al.

[11] Patent Number: 4,639,435

[45] Date of Patent: Jan. 27, 1987

[54] PHARMACEUTICAL COMPOSITION SUITABLE FOR INTESTINAL ADMINISTRATION

[75] Inventors: Setsuro Fujii, Toyonaka; Touru Yokoyama, Tokyo; Kouji Ikegaya, Higashi-Murayama; Nobuo Yokoo; Masahiko Nagakura, both of Sayama, all of Japan

[73] Assignee: Kowa Co., Ltd., Nagoya, Japan

[21] Appl. No.: 625,231

[22] Filed: Jun. 27, 1984

[30] Foreign Application Priority Data

Jun. 29, 1983 [JP] Japan ................................ 58-116089

[51] Int. Cl.$^4$ .................... A61K 37/30; A61K 37/558
[52] U.S. Cl. ........................................ 514/11; 514/10; 514/12; 514/808
[58] Field of Search .................... 260/112.5 R; 514/11, 514/10, 12, 808

[56] References Cited

FOREIGN PATENT DOCUMENTS 0071433 9/1983 European Pat. Off. .
0098713 1/1984 European Pat. Off. .

OTHER PUBLICATIONS

Chem. Abstr. vol. 95, (1981) 209657a.

Primary Examiner—Delbert R. Phillips
Attorney, Agent, or Firm—Oblon, Fisher, Spivak, McClelland, & Maier

[57] ABSTRACT

A pharmaceutical composition is disclosed which comprises a physiologically active substance possessing peptide bonds in its structure and being inactivable by digestive enzymes, the active substance being other than insulin, and a synthetic chymotrypsin inhibitor. The composition is particularly suitable for intestinal absorption of the active substance.

3 Claims, No Drawings

PHARMACEUTICAL COMPOSITION SUITABLE FOR INTESTINAL ADMINISTRATION

BACKGROUND OF THE INVENTION

Field of the Invention

This invention relates to a novel pharmaceutical composition suitable for intestinal absorption.

DESCRIPTION OF THE PRIOR ART

Discussion of the Background

A number of natural substances have recently come into use for medicinal purposes. However, since most of these natural substances possess peptide bonds in their configurations, they are readily decomposed and denatured by the action of digestive enzymes, when administered orally, and hence do not exert their inherently desired effects. Although it is reported that a certain level of physiological effectiveness can be obtained by administration of physiologically active substances in larger doses, the active substances are rather expensive and necessarily suffer economical disadvantages. The larger doses just mentioned are limited solely to some special cases.

Because of the foregoing problem, these physiologically active substances are usually administered by an injection route. Such route of administration gives patients pain and experiences other inconveniences. Consequently, this lends an impetus to the development for a more advanced form of administration of the physiologically active substances.

Under these circumstances, oral preparations and suppositories have recently been reported which contain a specific type of physiologically active substance and a naturally occurring trypsin inhibitor. However, the two dosage forms are not still practicable in that the active substance is hardly absorbed.

With the above noted difficulties in view, the present inventors have conducted intensive research to find that an orally dosable insulin preparation is obtainable when a synthetic chymotrypsin inhibitor of a phenyl ester type is formulated with insulin. This finding has become the subject matter of an earlier patent application [Japanese Patent Publication (Kokai) No. 21622/1983].

Through further research efforts made to determine the influences of such chymotrypsin inhibitor on the intestinal absorption of various drugs, it has now been discovered that combined use of a peptide bond-possessing, physiologically active substance and a synthetic chymotrypsin inhibitor allows the active substance to be absorbed intestinally, i.e., orally.

SUMMARY OF THE INVENTION

This invention provides a novel pharmaceutical composition suitable for intestinal absorption which ensures oral administration of a physiologically active substance with satisfactory results, which active substance is difficult to be orally administered with the existing prior art techniques.

This and other objects and advantages of the invention can be attained by the provision of a pharmaceutical composition suitable for intestinal absorption, which comprises a physiologically active substance possessing peptide bonds in its structure and being inactivable by digestive enzymes, said active substance being other than insulin, and a synthetic chymotrypsin inhibitor.

DETAILED DESCRIPTION OF THE PREFERRED EMBODIMENTS

As a synthetic chymotrypsin inhibitor eligible for the practive of this invention, use may be made of benzoylpiperazine ester compounds of a the following formula (I)

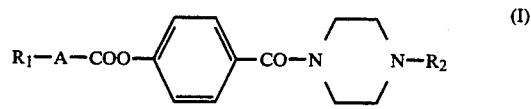

wherein
A is a single bond, or an alkylene, vinylene, —O-alkylene or methine group;

$R_1$ is a bicyclic carbocyclic residue which may partly be saturated and may optionally be substituted by at least one member of the class consisting of lower alkyl, lower alkoxy, oxo and nitro groups and halogen atoms; a fluorene residue which may optionally have an oxo group; a fluorenylidene group; an anthracene residue; a phenanthrene residue which may partly be saturated and may optionally be substituted by at least one lower alkyl group; a benzofuran or thianaphthene residue which may optionally be substituted by at least one member of the class consisting of lower alkyl and lower alkoxy groups; a benzopyran or benzazine residue which may partly be saturated and may optionally be substituted by at least one member of the class consisting of oxo and phenyl groups; a phthalimide residue; a benzodiazone residue; an isoxazole residue which may optionally be substituted by at least one member of the class consisting of lower alkyl and phenyl groups; an alkylenedioxybenzene residue; or a xanthene residue, and $R_2$ is a loweralkyl, cycloalkyl, cycloalkylalkyl or aralkyl group.

The methods of producing the compounds of the formula (I) and their chymotrypsin inhibitory activity characteristics have been described in Japanese Patent Application No. 109192/1982 and in Japanese Patent Application filed Apr. 28, 1983. A typical production method is as follows:

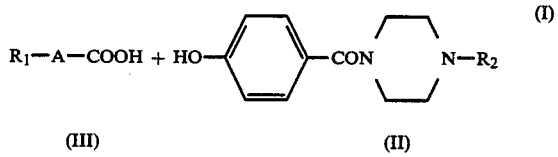

wherein the symbols $R_1$, A and $R_2$ are as defined above with respect to the formula (I) above.

Thus, the benzoylpiperazine chymotrypsin inhibitors of the formula (I) can be produced in conventional manner by esterifying 4-substituted piperazinocarbonylphenols of the formula (II) with carboxylic acids of the formula (III).

In effecting the esterification reaction, it is advantageous to react reactive derivatives of the compounds of the formula (III), such as acid halogenides, acid anhydrides, mixed acid anhydrides, active esters or azides, with the compounds of the formula (II). Alternatively, the compounds of the formula (II) may be reacted with the compounds of the formula (III) in the presence of a dehydrating agent such as dicyclohexylcarbodiimide.

The thus-obtained compounds of the formula (I) can further be converted in conventional manner to inorganic acid salts formed for example with hydrochloric acid, sulfuric acid, phosphoric acid and hydrobromic acid, or organic acid salts formed for example with acetic acid, propionic acid, maleic acid, fumaric acid, tartaric acid, oxalic acid, citric acid, methanesulfonic acid, benzenesulfonic acid and toluenesulfonic acid.

The synthetic chymotrypsin inhibitors can be used in the free base form or in the form of appropriate acid addition salts. These inhibitors may be used either alone or in combination with two to several thereof, depending upon the inhibitory activity level of each inhibitor.

The synthetic chymotrypsin inhibitors are compounds having substantially low toxicity. For instance, their acute toxicity values ($LD_{50}$ values) in mice are, for oral administration, within the range of about 5 to 10 g/kg and, for intravenous administration, within the range of about 300 to 400 mg/kg. Moreover, the compounds exhibit very high chymotrypsin inhibitory activity with about $10^{-6}$ to $10^{-8}$ M (molecule per liter) in a 50% inhibition concentration ($IC_{50}$).

A physiologically active substance, which is an active ingredient in a pharmaceutical composition of the invention, includes those which possess peptide bonds in their structure and which, upon exposure to various proteolytic enzymes present in the digestive tract, are inactivated by decomposition or denaturation. When administered orally, therefore, the active substances cannot be absorbed or cannot produce their therapeutic effects to a satisfactory extent. More particularly, the active substances range from peptides having a molecular weight of several hundred to macromolecular proteins having a molecular weight of around 1 million and preferably have a molecular weight of about 500 to about 300,000.

Eligible examples of such physiologically active substances are enzymes, such as lysozyme, seaprose, serratiopeptidase, pronase, lipase, elastase, esterase, streptokinase, urokinase, plasmin, plasminogen activators, streptodornase and hyaluronidase; peptide hormones, such as calcitonin, prolactin, adrenocorticotropin, thyrotropin, growth hormone, gonadotropic hormone, oxytocin, vasopressin, gastrin, tetragastrin, pentagastrin, glucagon, secretin, pancreozymin, substance P and gonadotropin; blood components, such as immunoglobulin, fibrinogen, albumin and blood coagulation factors; Krestin; aprotinin; and interferon.

As the physiologically active substances, there may also be used purified extracts of natural origin and their chemical modifications as well as products obtained by tissue culture and products obtained by cultivating microorganisms or cells rendered productive by genetic engineering techniques.

The pharmaceutical composition according to the invention is preferably administered in any form in which a synthetic chymotrypsin inhibitor and a physiologically active substance are allowed to coexist in the intestine, for example, in the form of tablets, granules or capsules, with both ingredients provided with an enteric coating either separately or compositely. The composition may also be administered rectally in the form of suppositories prepared by adding both ingredients to a suppository base in ordinary use. Where desirable, these dosage forms may be added with various pharmaceutically acceptable additives, such as excipients and emulsifiers.

The dose of the physiologically active substance is preferably 0.0001 to 1 time the dose if such substance is administered orally in the prior art and preferably 0.5 to 10 times the dose if such substance is administered by injection in the prior art. The amount of the synthetic chymotrypsin inhibitor should preferably be constant irrespective of the kind of the above physiologically active substance, and its preferred daily dose is in the range of 200 to 2,000 mg.

Several pharmaceutical compositions for intestinal absorption according to this invention were tested and evaluated with respect to their effectiveness, with the results given below.

In each test example, 1-isopropyl-4-[4-(1,2,3,4-tetrahydronaphthoyloxy) benzoyl]piperazine methanesulfonate (hereinafter referred to as "sample") was used as a synthetic chymotrypsin inhibitor.

The sample and a physiologically active substance were administered in the respective doses tabulated in Table I below in order to determine the absorption of the physiologically active substance from the intestine.

TABLE 1

| Test No. | Animal used | Physiologically active substance Substance tested | Dose (mg/kg) | Dose of sample (mg/kg) |
|---|---|---|---|---|
| 1 | Rat | Serratiopeptidase | 60 | 50 |
| 2(a) | " | Seaprose | 30 | 100 |
| (b) | " | " | 30 | 25 |
| 3 | " | Elastase | 4 | 50 |
| 4 | " | Fusarium protease | 30 | 50 |
| 5 | " | Sfericase | 30 | 50 |
| 6 | " | Human plasminogen | 10 | 50 |
| 7 | " | Urokinase | 50,000 [U/kg] | 50 |
| 8 | " | Kallikrein | 10,000 [U/kg] | 50 |
| 9 | " | Immunoglobulin G | 10 | 50 |
| 10 | " | Calcitonin | 100 [U/kg] | 20 |

Procedure

Wistar strain rats (weighing about 300 g) in groups each having 4 animals were laparotomized under anesthesia with urethane, and an aqueous solution of each physiologically active substance given in Table 1 and the sample was administered by means of a needle of injection with the duodenum at a site 2 cm below the pylorus being ligated.

After administration, blood was sampled at timed intervals from the inferior vena cava and assayed for the activity of the physiologically active substance in blood.

When the physiologically active substances were enzymes, use was made of the substrates given in Table 2 below.

In the case of plasminogen, streptokinase was added, and then the hydrolyzing activity of the substrate (Boc-Val-Leu-Lys-MCA) was measured to calculate the activity of plasminogen. For immunoglobulin G. PITC-bound human immunoglobulin G (Cappel Lab.) was used and assayed by the fluorescence method. In the case of calcitonin, a group of 5 SD strain rats (weighing 90 to 100 g) was used, and the animals were laparotomized under pentobarbital anesthesia, followed by administration. Blood samples were taken from the caudal vein 1 and 2 hours after administration and assayed for the serum calcium concentration using a calcium assay reagent (Iatron). The results were expressed in terms of the percentage of reduction in the serum calcium concentration relative to the concentration before administration (=100).

Results

The results obtained are shown in Table 2. Each value is the value after subtraction of the value found before administration. For each of the test results, the values shown in the upper row are those found without any sample added.

TABLE 2

| Test No. | Substrate | Activity (μM AMC/30 min.) | | | |
|---|---|---|---|---|---|
| | | 15 min. | 30 min. | 60 min. | 120 min. |
| 1 | Boc—Val—Leu—Lys—MCA | 0.05 ± 0.01 | 0 | 0.15 ± 0.02 | 0.40 ± 0.04 |
| | | 0.25 ± 0.01 | 0.15 ± 0.01 | 0.25 ± 0.01 | 0.45 ± 0.04 |
| 2(a) | Suc—Leu—Leu—Val—Tyr—MCA | 0.02 ± 0.01 | 0.05 ± 0.02 | 0.11 ± 0.05 | 0.20 ± 0.08 |
| | | 3.39 ± 0.86 | 3.98 ± 1.93 | 1.39 ± 0.99 | 0.55 ± 0.29 |
| 2(b) | Suc—Leu—Leu—Val—Tyr—MCA | — | — | — | — |
| | | 1.93 ± 0.90 | 0.41 ± 0.17 | 0.13 ± 0.05 | 0.25 ± 0.07 |
| 3 | Suc—Ala—Pro—Ala—MCA | 0 | 0 | 0 | 0 |
| | | 0.54 ± 0.16 | 1.26 ± 0.01 | 0.19 ± 0.11 | 0.07 ± 0.03 |
| 4 | Suc—Leu—Leu—Val—Tyr—MCA | 2.03 ± 1.54 | 0.91 ± 0.46 | 0.97 ± 0.57 | 1.16 ± 0.66 |
| | | 19.96 ± 7.14 | 8.77 ± 3.68 | 1.72 ± 0.83 | 0.62 ± 0.24 |
| 5 | Suc—Leu—Leu—Val—Tyr—MCA | 0.13 ± 0.08 | 0.08 ± 0.03 | 0.14 ± 0.07 | 0.23 ± 0.08 |
| | | 0.81 ± 0.18 | 0.84 ± 0.53 | 0.65 ± 0.44 | 0.21 ± 0.09 |
| 6 | Boc—Val—Leu—Lys—MCA | 3.60 ± 0.55 | 3.60 ± 0.70 | 4.30 ± 0.95 | 4.40 ± 0.95 |
| | | 5.10 ± 0.60 | 5.60 ± 0.80 | 4.75 ± 0.35 | 4.25 ± 0.65 |
| 7 | Glt—Gly—Arg—MCA | 0.14 ± 0.04 | 0.10 ± 0.05 | 0.03 ± 0.02 | 0.06 ± 0.04 |
| | | 0.31 ± 0.09 | 0.64 ± 0.24 | 0.34 ± 0.14 | 0.24 ± 0.07 |
| 8 | Pro—Phe—Arg—MCA | 4.5 ± 0.7 | 5.5 ± 0.2 | 7.3 ± 2.1 | 15.6 ± 4.3 |
| | | 5.8 ± 1.1 | 5.6 ± 1.0 | 10.7 ± 0.9 | 14.0 ± 1.2 |
| 9 | | 0 | 0 | 0 | 2.00 ± 1.70 |
| | | 1.75 ± 0.85 | 1.50 ± 0.87 | 1.50 ± 0.50 | 3.50 ± 26.0 |
| 10 | | | | 9.9 ± 4.0(%) | 4.6 ± 3.5(%) |
| | | | | 2.23 ± 2.8(%) | 20.9 ± 4.9(%) |

The following examples are provided to further illustrate this invention, but it should be noted that the invention is not limited thereto.

In these examples, the following compounds of the formula (I) were used as chymotrypsin inhibitors.

$$R_1-A-COO-\text{[phenyl]}-CO-N\text{[piperazine]}N-R_2$$

| Examples | $R_1$ | A | $R_2$ |
|---|---|---|---|
| 1 | [1,2,3,4-tetrahydronaphthyl] | bond | iso-propyl |
| 2 | [1,2,3,4-tetrahydronaphthyl] | bond | cyclohexyl |
| 3 | [fluorenyl] | =CH— | iso-propyl |
| 4 | [naphthyl] | —CH$_2$— | iso-propyl |

EXAMPLE 1

(Tablet)

Lysozyme (300 mg) was mixed with 100 mg of a chymotrypsin inhibitor, followed by addition of an appropriate amount of each of crystalline cellulose, carboxymethylcellulose calcium, hydroxypropylcellulose and magnesium stearate. The whole mixture was tableted, and the resulting tablet was further provided with an enteric coating.

EXAMPLE 2

(Granules)

Globulin (500 mg) was mixed with 300 mg of a chymotrypsin inhibitor, followed by addition of an appropriate amount of each of crystalline cellulose, carboxymethylcellulose calcium and hydroxypropylcellulose. The whole mixture was granulated, and the resulting granules were provided with an enteric coating.

EXAMPLE 3

(Capsule)

Urokinase (100,000 units) was mixed with 200 mg of a chymotrypsin inhibitor, followed by addition of an appropriate amount of each of crystalline cellulose, talc and carboxymethylcellulose calcium. A gelatin capsule was filled with the whole mixture and then provided with an enteric coating.

EXAMPLE 4

(Tablet)

Using 50 units of kallikrein and 150 mg of a chymotrypsin inhibitor and following the procedure of Example 1, there was produced an enteric tablet.

What is claimed is:

1. A pharmaceutical composition suitable for intestinal absorption, comprising (i) a physiologically active substance which is at least one member selected from the group consisting of kallikrein and calcitonin, and (ii) 1-isopropyl-4-[4-(1,2,3,4-tetrahydronaphthoyloxy)-benzoyl] piperazine methanesulfonate.

2. The pharmaceutical composition 1, wherein the said physiologically active substance is kallikrein.

3. The pharmaceutical composition of claim 1, wherein the said physiologically active substance is calcitonin.

* * * * *